US009837256B2

(12) United States Patent
Baba

(10) Patent No.: US 9,837,256 B2
(45) Date of Patent: Dec. 5, 2017

(54) SIMULTANEOUS POSITIVE AND NEGATIVE ION ACCUMULATION IN AN ION TRAP FOR MASS SPECTROSCOPY

(71) Applicant: DH Technologies Development PTE Ltd., Singapore (SG)

(72) Inventor: Takashi Baba, Richmond Hill (CA)

(73) Assignee: DH Technologies Development Pte. Ltd., Singapore (SG)

(*) Notice: Subject to any disclaimer, the term of this patent is extended or adjusted under 35 U.S.C. 154(b) by 0 days.

(21) Appl. No.: 15/105,130

(22) PCT Filed: Nov. 18, 2014

(86) PCT No.: PCT/IB2014/002482
§ 371 (c)(1),
(2) Date: Jun. 16, 2016

(87) PCT Pub. No.: WO2015/097503
PCT Pub. Date: Jul. 2, 2015

(65) Prior Publication Data

US 2016/0322208 A1 Nov. 3, 2016

Related U.S. Application Data

(60) Provisional application No. 61/920,552, filed on Dec. 24, 2013.

(51) Int. Cl.
*H01J 49/26* (2006.01)
*H01J 3/00* (2006.01)
(Continued)

(52) U.S. Cl.
CPC ...... *H01J 49/0095* (2013.01); *H01J 49/0072* (2013.01); *H01J 49/062* (2013.01); *H01J 49/4225* (2013.01)

(58) Field of Classification Search
CPC .. H01J 49/0072; H01J 49/063; H01J 49/4225; H01J 49/107; H01J 49/423;
(Continued)

(56) References Cited

U.S. PATENT DOCUMENTS 5,783,824 A * 7/1998 Baba .................... H01J 49/423 250/281
7,358,488 B2 * 4/2008 Chernushevich ..... H01J 49/063 250/281
(Continued)

OTHER PUBLICATIONS

International Search Report and Written Opinion for PCT/IB2014/002482 dated Feb. 27, 2015.

*Primary Examiner* — David A Vanore

(57) ABSTRACT

A mass spectrometer ion reaction device, useful for performing ion-ion reactions (eg. ETD, PTR) is described. The device includes a plurality of non-linear rods, that form a pair of quadrupole rod sets. The device includes an axial passageway, that allows injections of ions of both polarities into the device, and a three dimensional trapping region. Anions and cations that are injected into the device are spatially separated into different trapping regions by a DC dipole electric field generated by a DC voltage source. The device also includes a plurality of lenses to confine, transmit or receive ions in/from the device.

14 Claims, 15 Drawing Sheets

(51) Int. Cl.

| | |
|---|---|
| ***H01J 49/00*** | (2006.01) |
| ***H01J 49/06*** | (2006.01) |
| ***H01J 49/42*** | (2006.01) |

(58) Field of Classification Search

CPC .. H01J 49/004; H01J 49/0045; H01J 49/0077; H01J 49/0095; H01J 49/0481; H01J 49/065; H01J 49/40; H01J 49/422; H01J 49/4295

USPC ....... 250/281, 282, 283, 288, 292, 290, 285, 250/287

See application file for complete search history.

(56) References Cited

U.S. PATENT DOCUMENTS 8,604,419 B2 * 12/2013 Nolting ............... H01J 49/0072 250/281
2005/0199804 A1 * 9/2005 Hunt .................. G01N 33/6848 250/290
2007/0057178 A1 * 3/2007 Chernushevich ..... H01J 49/107 250/288
2008/0128611 A1 * 6/2008 McLuckey .......... H01J 49/4225 250/283
2009/0014645 A1 * 1/2009 Chernushevich ... H01J 49/0077 250/292
2010/0072360 A1 * 3/2010 Green ................. H01J 49/0072 250/282
2011/0186724 A1 8/2011 Nolting et al.
2011/0266434 A1 11/2011 Li
2011/0284738 A1 * 11/2011 Berg ................... H01J 49/0072 250/283
2012/0112059 A1 * 5/2012 Sugiyama ............. H01J 49/004 250/282
2013/0122599 A1 * 5/2013 Brown ................ H01J 49/0045 436/86

* cited by examiner

10

SIMULTANEOUS POSITIVE AND NEGATIVE ION ACCUMULATION IN AN ION TRAP FOR MASS SPECTROSCOPY

RELATED APPLICATION

This application claims priority to U.S. Provisional Application No. 61/920,552, filed on Dec. 24, 2013, which is incorporated herein by reference in its entirety.

BACKGROUND

The present teachings are related to mass spectrometers and methods for performing mass spectroscopy, and particularly to ion reaction devices for use in mass spectroscopy that can provide simultaneous trapping of positive and negative ions.

Mass spectrometry is an analytical technique for determining the elemental molecules of test samples that has both quantitative and qualitative applications. For example, mass spectroscopy can be employed to identify unknown compounds, determine the composition of elements in a molecule, and determine the structure of a molecule by observing its fragmentation, as well as for quantifying the amount of a particular compound in a sample.

Ion-ion reactions are widely employed in mass spectroscopy. Some examples of such ion-ion reactions include electron transfer dissociation (ETD) of peptide/protein cations via reaction with reagent anions. ETD allows preferential backbone dissociation of protonated peptides/proteins without loss of translational modification. Proton transfer reaction (PTR) is another example of an ion-ion reaction, which can be employed to reduce the charge state of multiply protonated peptides/proteins without causing backbone dissociation. Conventional mass spectrometers in which ion-ion reactions are employed to generate product ions can have certain shortcomings. For example, the way by which the precursor and reagent ions are conventionally introduced into a mass spectrometer can lead to a reduction of duty cycle.

There is a need for enhanced systems and methods for introducing positive and negative ions (e.g., precursor cations and reagent anions) into a mass spectrometer.

SUMMARY

In one aspect, an ion reaction device for use in a mass spectrometer is disclosed, which comprises an ion injection inlet for receiving a plurality of ions and an ion ejection outlet through which ions can exit the device. The reaction device further includes a plurality of non-linear rods disposed relative to one another so as to provide an axial region configured to receive a plurality of anions and cations via said ion injection inlet, and a plurality of trapping regions in communication with the axial region in which said anions and cations can be confined. A DC voltage source is adapted to apply a DC voltage across at least two of said rods so as to generate an electric field within at least a portion of said axial region for spatially separating the received anions and cations and guiding the anions into one of said trapping regions and the cations into another one of said trapping regions.

In some embodiments, the non-linear rods are in the form of L-shaped rods. Each L-shaped rod can include a longitudinal portion and a transverse portion forming an angle relative to the longitudinal portion. The axial region of the reaction device can be spatially defined by the longitudinal portions of the rods. The plurality of trapping regions can comprise two trapping regions that are spatially defined by said transverse portions of the rods, wherein each of the trapping regions extends radially from a proximal opening in communication with the axial region to a distal opening.

In some cases, the L-shaped rods comprise a pair of quadrupole rod sets. The quadrupole rod sets can be stacked vertically relative to one another so as that each rod in one set is disposed below a respective rod of the other set and, in some cases, in substantial register therewith. The DC voltage source can be connected at each terminal thereof to two rods of one of said quadrupole pairs and to two rods of the other quadrupole pairs, where said two rods of one pair are vertically stacked relative to said two rods of the other pair, so as to generate a dipole electric field in at least a portion of said axial region. By way of example, the DC voltage source can be configured to generate a DC voltage in a range of about 3 V to about 7 V.

In some embodiments, the ion reaction device can further include first and second lenses, wherein one of the lenses is disposed in proximity of the distal opening of one of the trapping regions and the other one of the lenses is disposed in proximity of the distal opening of the other trapping region, said lenses being adapted for application of DC bias voltages thereto for facilitating trapping of the anions and cations in the respective one of said trapping regions.

In some embodiments, the ion reaction device can further include a third lens disposed upstream of said plurality of rods and adapted for application of a DC voltage thereto. By way of example, the third lens can be in the form of a plate having an orifice, which forms the ion injection inlet of the reaction device.

In some embodiments, the ion reaction device can further include a fourth lens disposed downstream of said plurality of rods and adapted for application of a DC voltage thereto. By way of example, the fourth lens can include a plate having an orifice, which forms the ion ejection outlet of the reaction device.

In some embodiments, the ion reaction device can further include a fifth lens disposed in said axial region in proximity to said proximal openings of said trapping regions. The application of a DC bias voltage to the fifth lens can help in confining the ions (anions and the cations) in the respective trapping regions.

The ion reaction device can include a first RF source for applying RF voltages to the rods to generate RF fields that are configured to provide radial confinement of the anions and cations, e.g., as they propagate through the axial passage. Further, the ion reaction device can include a second RF source for applying RF voltages to the rods to generate RF fields that are configured to provide axial confinement of said anions and cations. In some embodiments, the first and second RF sources are configured to apply RF voltages having different frequencies to the rods. In some other embodiments, the first and second RF sources are configured to apply RF voltages having the same frequency to the rods.

In a related aspect, a mass spectrometer is disclosed, which comprises a plurality of ion sources, wherein at least one of said sources is adapted to generate anions and another of said sources is adapted to generate cations, and an ion reaction device configured to receive said anions and cations. The ion reaction device includes an ion injection inlet for receiving a plurality of ions and an ion ejection outlet through which ions can exit the device, a plurality of non-linear rods disposed relative to one another so as to provide an axial region configured to receive a plurality of anions and cations via said ion injection inlet, and a plurality of trapping regions in communication with the axial region in which said anions and cations can be simultaneously confined, and a DC voltage source adapted to apply a DC voltage across at least two of said rods so as to generate an electric field within at least a portion of said axial region for spatially separating the received anions and cations and guiding the anions into one of said trapping regions and the cations into another one of said trapping regions.

In some embodiments, a DC deflector, e.g., a quadrupole DC deflector, can be disposed upstream of the reaction device, where the deflector has first and second inlet ports for receiving, respectively, said anions and cations from the ion sources and having an outlet port in communication with said reaction device. The DC deflector is configured to guide said received anions and cations to said outlet port, e.g., as a merged ion beam for delivery to the downstream reaction device. The deflector simultaneously deflects both anions and cations.

In some embodiments, the mass spectrometer can further include a quadrupole lens disposed between the DC deflector and the reaction device for selecting cations and anions having an m/z ratio in a desired range, or a specific m/z value.

In some embodiments, the mass spectrometer can further include a first quadrupole filter disposed between the source for generating anions and said DC deflector for selecting anions having an m/z ratio in a desired range (or a specific value) for delivery to the DC deflector. In some such embodiments, a second quadrupole filter can be disposed between the source for generating cations and the DC deflector for selecting cations having an m/z ratio (or a specific m/z value) in a desired range for delivery to said DC deflector.

Further understanding of various aspects of the invention can be obtained by reference to the following detailed description in conjunction with the associated drawings, which are described briefly below.

DETAILED DESCRIPTION

The present teachings are generally related to mass spectrometers and methods of performing mass spectroscopy. A mass spectrometer according to the present teachings can include an ion reaction device (herein also referred to as a chimera trap) that employs a DC dipole field to guide anions and cations received from one or more upstream ion sources into different trapping regions. The trapped anions and cations can be subsequently released and mixed. As discussed in more detail below, the mixing of the anions and the cations can result in ion-ion interactions, which can generate product ions for analysis by downstream components of the spectrometer.

The various terms are used herein consistent with their ordinary meanings in the art. The term "about" is used to herein to denote a variation of at most 5%.

Figure 1:
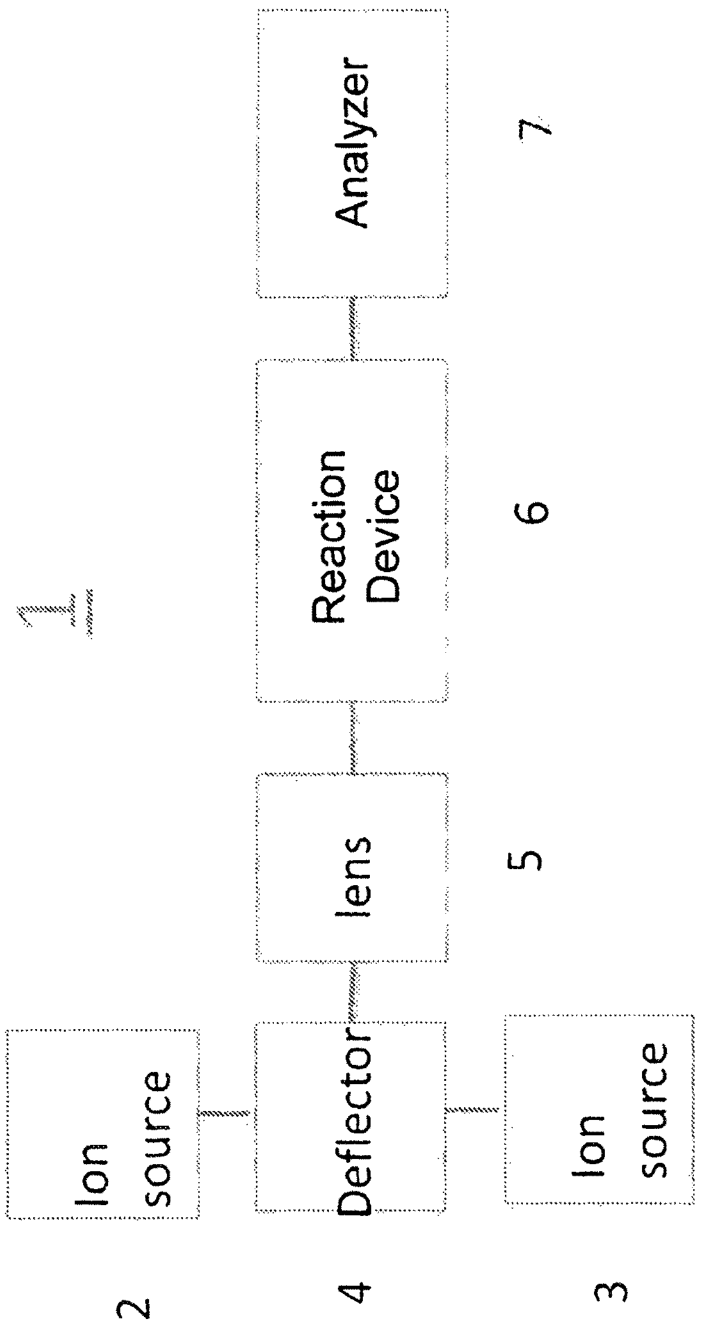
FIG. 1 is a block diagram depicting a mass spectrometer according to an embodiment of the present teachings, FIG. 2A schematically depicts a plurality of L-shaped rods in an ion reaction device according to the present teachings, FIG. 2B schematically depicts an ion reaction device according to the present teachings.

FIG. 1 schematically depicts a mass spectrometer 1 according to an embodiment of the present teachings, which includes a plurality of ion sources 2 and 3 for generating ions of different charge polarity. In one embodiment, the ion source 2 generates anions, e.g., anions of a reagent molecule, and the ion source 3 generates cations, e.g., cations of a precursor molecule. An ion deflector 4 receives the ions from the ion sources 2 and 3, e.g., via multiple inlet ports thereof, and merge the ions into an ion beam that is received by a downstream ion focusing device 5, e.g., a quadrupole ion lens, which radially focuses the ions. An ion reaction device 6 according to the present teachings and discussed in more detail below receives the ion beam including ions of different polarities from the ion lens 5. The reaction unit employs a DC dipole electric field to spatially separate the ions of different polarity and to transfer the cations and anions into separate trapping regions. In the separate trapping regions, the ions are trapped at RF potential minima so that dissociating excitation by the RF fields is reduced. Subsequently, the trapped ions can be released and mixed. In some embodiments, the mixing of the ions can lead to ion-ion interactions, such as electron transfer dissociation (ETD) or proton transfer reaction (PTR), to generate product ions. The product ions can then be extracted from the reaction unit and guided to a mass analyzer 7. The mass analyzer can include a variety of elements including a detector for detecting the ions and generating information for obtaining a mass spectrum of the product ions.

Figure 2A:
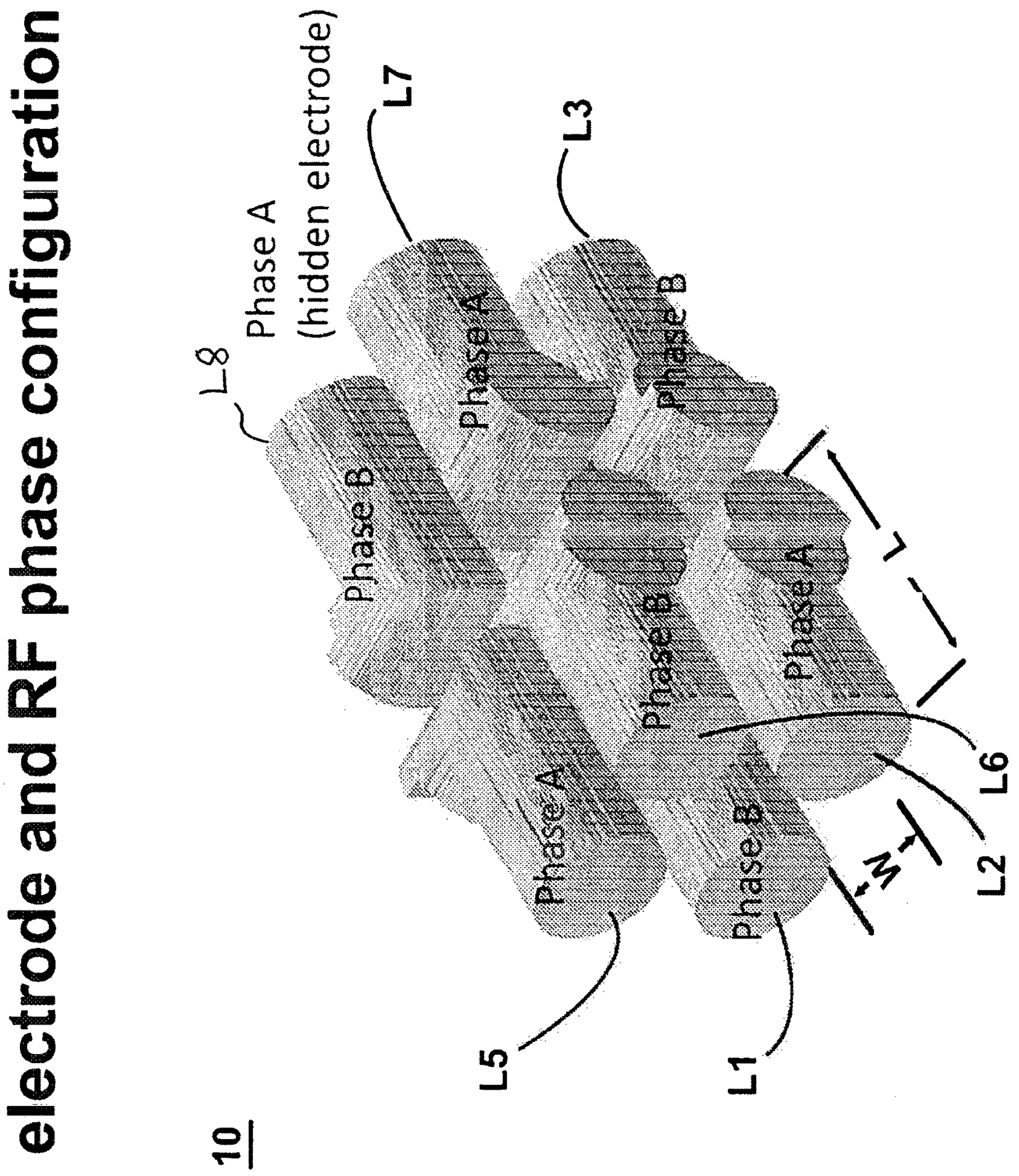
Figure 2B:
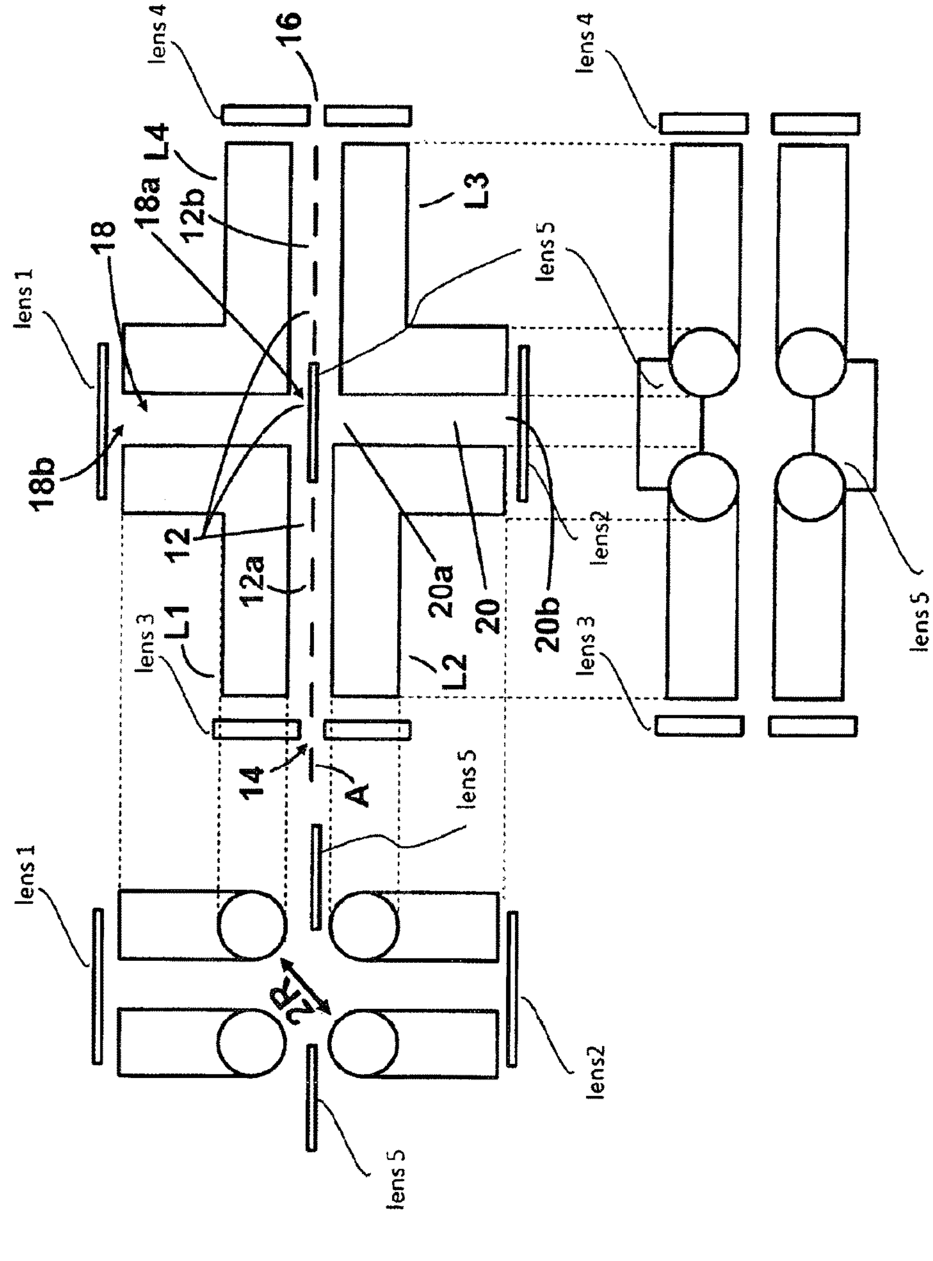

With reference to FIGS. 2A, and 2B, an ion reaction device 10 for use in a mass spectrometer according to an embodiment of the present teachings includes eight generally L-shaped rods (herein also referred to as electrodes) L1, L2, L3, L4, L5, L6, L7, and L8 that are arranged as two pairs of lower electrodes (L1-L4) and two pairs of upper electrodes (L5-L8) stacked relative to one another to provide an axial ion passage region (axial passageway, or axial passage) 12 through which ions can pass, and two three-dimensional ion trapping regions (herein also referred to as trapping ports) 18 and 20 in which ions of different polarity can be simultaneously trapped, as discussed in more detail below. The axial passageway 12 includes an ion injection portion (herein also referred to as an ion injection port) 12*a* that receives a plurality of ions through an ion injection port 14 of the reaction device and an ion ejection portion (herein also referred to an ion ejection port) 12*b* through which ions can exit the reaction through an ion ejection port 16.

Each L-shaped electrode includes a longitudinal portion that extends along a longitudinal axis (A) (herein also referred to as the injection axis) of the reaction device and a transverse portion that extends substantially perpendicular to the longitudinal portion. In some embodiments, each electrode can have a longitudinal dimension (i.e., a dimension along the longitudinal axis A) (L) in a range of about 5 mm or longer, and a transverse dimension (i.e., a dimension perpendicular to the longitudinal axis A) (W) in a range of about 5 mm or longer. In some embodiments, each pair of the lower electrodes (L1-L4) and each pair of the upper electrodes (L5-L8) are radially separated from the respective electrode of that pair by a distance (2R), where R is in a range of about 2 mm to about 10 mm. In this embodiment, the L-shaped rods exhibit a sharp 90-degree bend. In other embodiments, the bend may include a smooth radius of curvature. In yet other embodiments, non-linear rods having other shapes can be employed. For example, the rods can include two portions forming an angle other than 90 degrees at a connecting junction.

The trapping region 18 is in communication with the axial passageway 12 via a proximal opening 18*a*, and extends radially to a distal opening 18*b*. The trapping region 20 is in communication with the axial passageway 12 via a proximal opening 20*a*, and extends radially to a distal opening 20*b*.

With continued reference to FIG. 2B, the reaction device 10 further includes a plurality of lenses 1, 2, 3, 4, and 5. The lens 1 is in the form of a conductive plate and is disposed in proximity of the distal opening 18*b*. As discussed in more detail below, the lens 1 can be biased (e.g., via application of an appropriate DC voltage) to block the exit of the trapped ions from the trapping port 18. The lens 2 is also in the form of a conductive plate and is disposed in proximity of the distal opening 20*b* of the ion trapping port 20. The lens 2 can be biased (e.g., via application of an appropriate DC voltage) to block the exit of the trapped ions from the trapping port 20. The lens 3 is in the form of an electrically conductive plate having a central orifice, which functions as the ion injection port 14 through which ions can pass to enter the injection port 12*a* of the axial region 12. The lens 4 is also in the form of an electrically conductive plate having a central orifice, which functions as the ion ejection port 16 through which ions (e.g., product ions as discussed below) can exit the reaction device 10 after passage through the ejection port 12*b*. As discussed in more detail below, during various phases of ion processing, the lenses 3 and 4 can be biased (e.g., by application of appropriate DC voltages), or held at the ground electric potential, to facilitate axial trapping of the ions in the space between the electrodes or to facilitate the injection and ejections of ions into and out of the reaction device 10. A lens 5 in the form of a plate is disposed in a central region of the passageway 12 in proximity to the proximal ports 18*a* and 20*a* of the trapping regions 18 and 20. As discussed in more detail below, the lens 5 can be held at the ground potential during certain stages of ion processing and can be biased (e.g., by application of an appropriate DC voltage) during other stages, e.g., to help contain the trapped ions within the trapping ports 18 and 20, as discussed in more detail below.

Figure 3A:
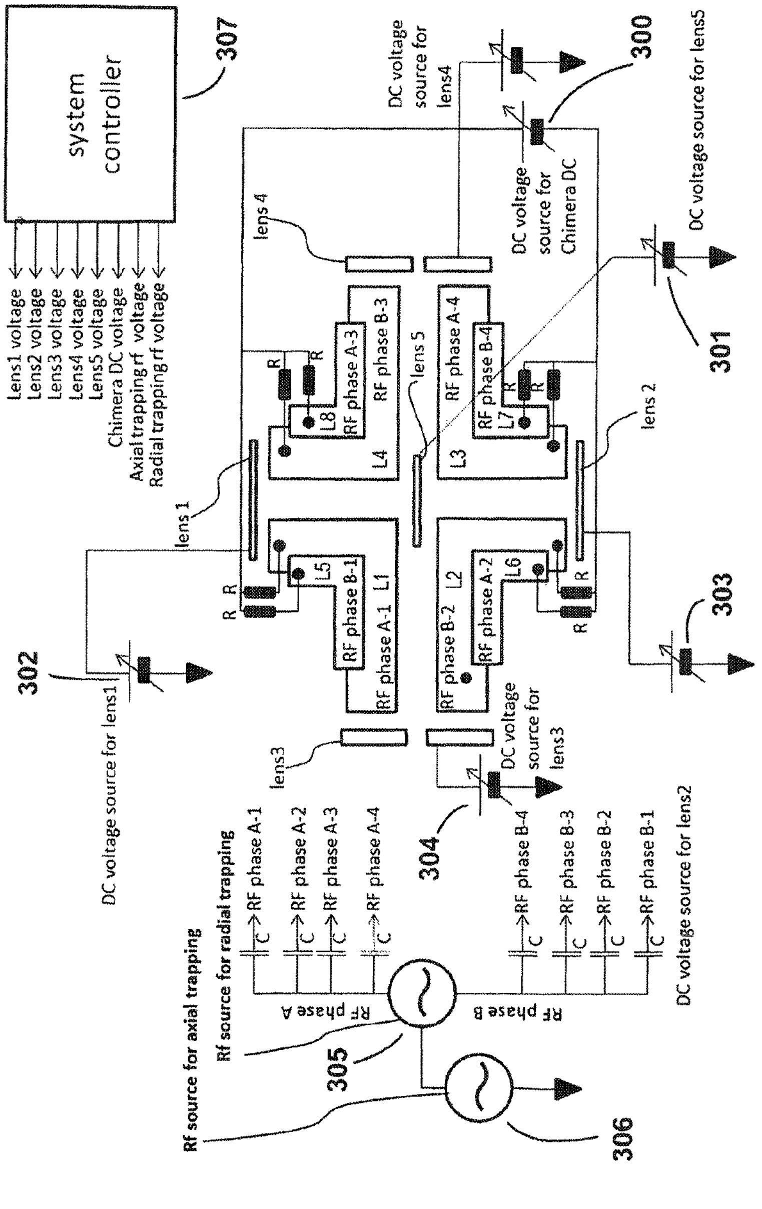
FIG. 3A depicts a circuit employed in an embodiment of the present teachings for applying DC and RF voltages to various components of the ion reaction device, FIG. 3B schematically depicts exemplary internal hardware of the system controller shown in FIG. 3A, FIG. 4A schematically depicts an embodiment of an ion reaction device according the present invention during an ion accumulation phase.

With reference to FIG. 3A, the reaction device 10 further includes a DC voltage source 300 that is electrically connected at one terminal thereof to the electrodes L1, L4, L5 and L8 (herein referred to collectively as a first set of electrodes), and at another terminal to the electrodes L2, L3, L6 and L7 (herein referred to collectively as a second set of electrodes) so as to apply a DC potential difference between the first and the second electrode sets to generate a dipolar DC electric field in the axial passageway so as to spatially separate the ions of different polarities as they pass through the injection port and guide the ions of one polarity into one of the trapping regions and the ions of the opposite polarity into the other trapping region. In addition, the DC bias voltage can provide a stable trapping potential in the trapping regions 18 and 20. In some embodiments, the DC voltage applied across the first and second electrode sets can be, e.g., in a range of about 3 volts (V) to about 7 V.

With continued reference to FIG. 3A, a DC voltage source 301 can apply a DC voltage to the lens 5, a DC voltage source 302 can apply a DC voltage to the lens 1, a DC voltage source 303 can apply a DC voltage to the lens 2, and a DC voltage source 304 can apply a DC voltage to the lens 3. In some embodiments, the DC voltages applied to the lenses 1, 2, 3, 4, and 5 can be in a range of about −10 V to about +10 V. Further, an RF source 305 applies RF voltages to the electrodes L1-L8 so as to provide radial (i.e., in a direction perpendicular to the longitudinal axis (A) shown in FIG. 2B) confinement (trapping) of the ions, e.g., during the passage of the ions through the axial passageway 12. Another RF source 306 can apply an RF voltage to the electrodes L1-L8 so as to provide axial trapping of the ions during certain phases of ion processing. In this embodiment, while the phases of the RF voltages applied to the electrodes L1-L8 by the RF source 305 can differ to provide an AC electric field configured for radial trapping of the ions, the phases of RF voltages applied to the electrodes L1-L8 by the RF source 306 can be the same.

In some embodiments, the frequency of the RF voltages applied by the RF source 305 to the electrodes can be in a range of about 200 kHz to about 1 MHz, and the root-mean-square (rms) amplitude of the voltage can be in a range of about 50 to about 200 volts. Further, the frequency of the RF voltage applied by the RF source 306 to the electrodes can be in a range of about 200 kHz to about 1 MHz, and rms amplitude of the voltage can be in a range of about 50 V to about 200 V.

A system controller 307 controls the application of the RF and DC voltages to the electrodes L1-L8 as well as the lenses 1-5. The controller 307 can adjust the voltages applied to these elements during different phases of ion processing to facilitate injection of ions into the reaction device 10, the trapping of the ions, their mixing, and the ejection of the product ions, as discussed in more detail below.

Figure 3B:
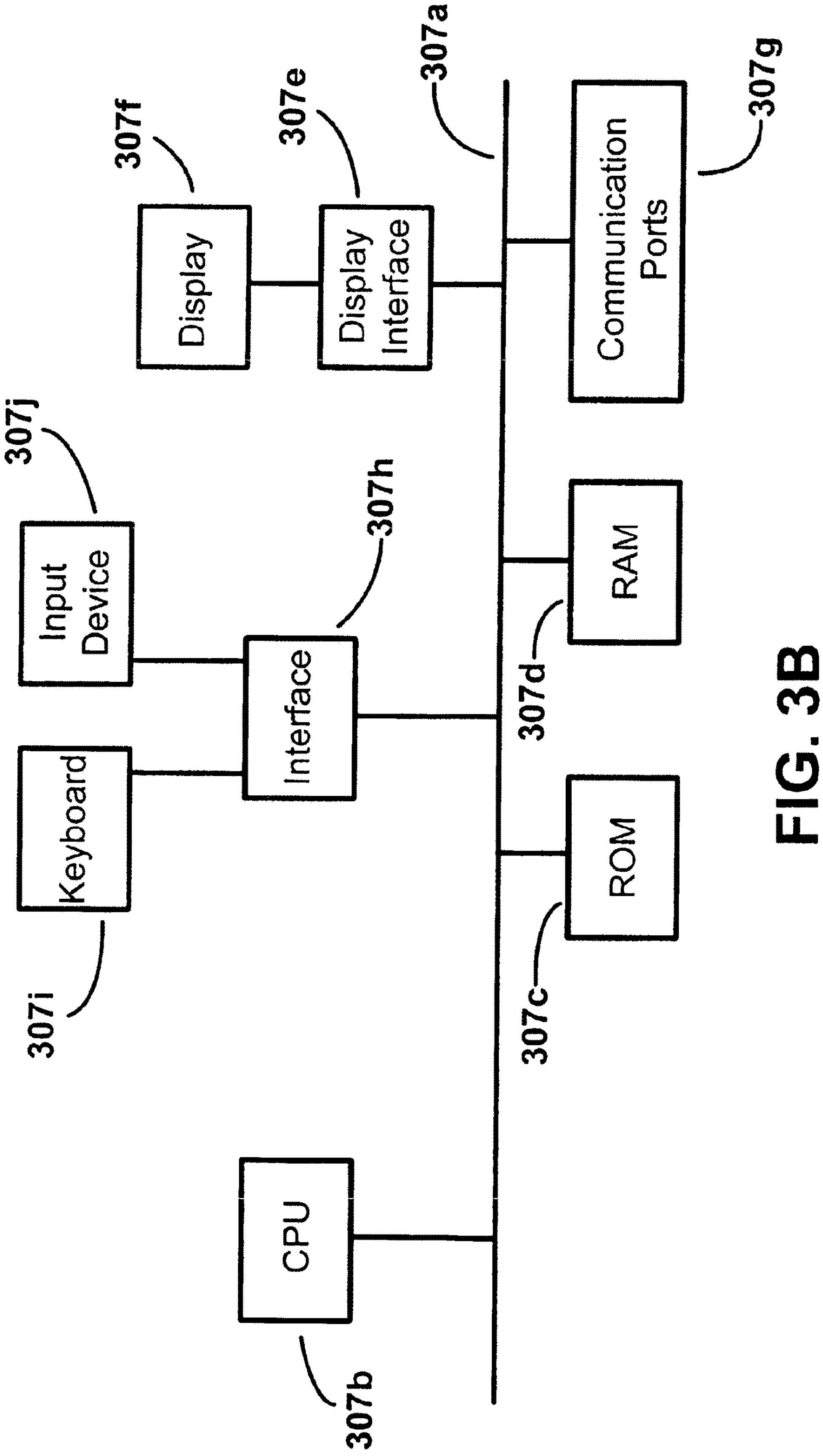

By way of further illustration, FIG. 3B depicts a block diagram of exemplary internal hardware that may be used to implement the system controller 307. A bus 307*a* interconnects the other illustrated components of the hardware. A central processing unit (CPU) 307*b* executes instructions for performing various steps of ion processing as discussed herein. The instructions can include adjusting DC and RF voltages applied to the rods and the lenses of the ion reaction device in accordance with the present teachings. Read only memory (ROM) 307*c* and random access memory (RAM) 307*d* can be utilized to store the instructions. An optional interface 307*e* can allow information from the bus 307*a* to be displayed on the display 307*f*. The communication ports 307*g* allow communication with external devices. The hardware may also include an interface 307*h* that can allow the receipt of data from input devices such as a keyboard 307*i* or other input device 307*j*.

Figures 4A, 4B:
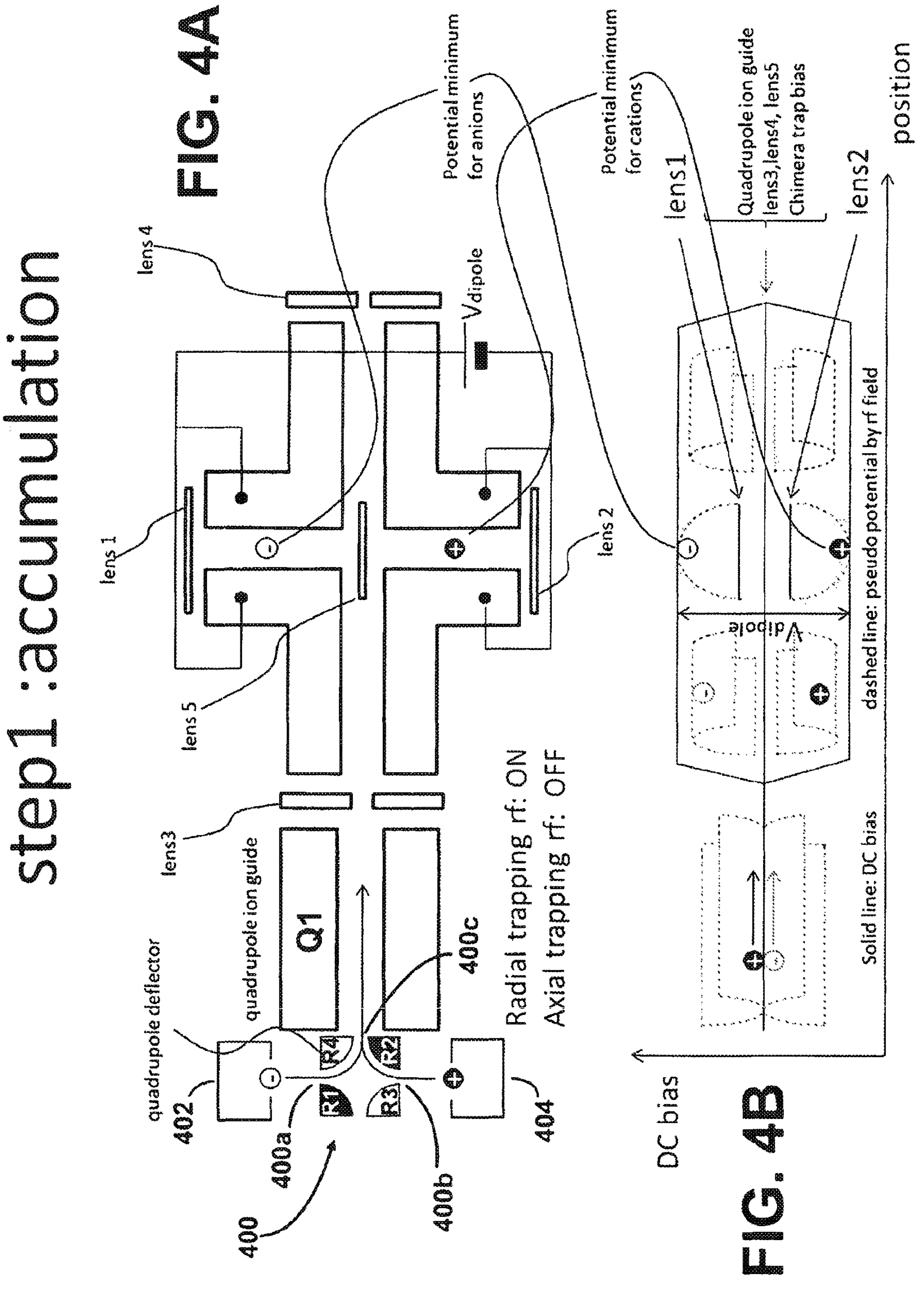
FIG. 4B shows RF and DC potential profiles employed in the accumulation phase depicted in FIG. 4A.

In some embodiments, a plurality of upstream deflectors and ion guides are employed to introduce ions from a plurality of ion sources, e.g., a source generating reagent ions and a source generating precursor ions, into the reaction device 10. By way of example, FIG. 4A schematically depicts an upstream quadrupole DC deflector 400 having two inlet ports 400*a* and 400*b* for receiving ions from two different ion sources. In this embodiment, the inlet port 400*a* receives a plurality of negative ions (e.g., reagent anions) from a negative ion source 402 and the inlet port 400*b* receives a plurality of positive ions (e.g., precursor cations) from a positive ion source 404. The quadrupole DC reflector 400 includes four rods R1, R2, R3, and R4 that are disposed relative to one another to provide a passage therebetween through which the ions can flow. A plurality of DC voltages applied to the rods of the DC deflector can generate a quadrupole electric field in the region between the rods that is configured to deflect both the positive and the negative ions to an exit port 400*c*. In this way, the positive and negative ions merge and exit the quadrupole deflector 400 concurrently into a downstream quadrupole ion guide Q1. It should be understood that the use of the DC quadrupole deflector 400 is optional, and in other embodiments, other techniques for introducing positive and negative ions into the reaction device can be utilized.

A variety of different types of ion sources can be employed. Some examples of suitable ion sources include, without limitation, an electrospray ionization ("ESI") source, a desorption electrospray ionization ("DESI") source, or a sonic spray ionization ("SSI") source, an atmospheric pressure chemical ionization (APCI) source, and a chemical ionization (CI) source, among others.

With continued reference to FIG. 4A, in use, in an initial step 1 (accumulation step) the quadrupole ion guide Q1 receives the merged positive and negative ions from the quadrupole deflector 400. By application of appropriate RF voltages to the rods of the quadrupole ion guide Q1, it can be configured to function as an ion guide for transmission of ions indiscriminately (e.g., transmission of ions having m/z ratios over a wide range) or it can be configured to function as a mass selective filter to allow transmission of ions having an m/z ratio only in a desired range (or at a specific value) and remove ions having m/z ratios outside that range. In some embodiments, the Q1 ion guide is configured to confine radially substantially all ions received from the ion sources and transmit those ions to the subsequent downstream elements. For example, as depicted in FIG. 4B, the RF voltages applied to the rods of the ion guide Q1 can generate pseudo potentials for the positive and negative ions with minima close to the central axis of the guide to radially confine the ions in a region close to the central axis. In this embodiment, the ions passing through the Q1 ion guide pass through the lens 3 to enter the reaction device.

Figure 5:
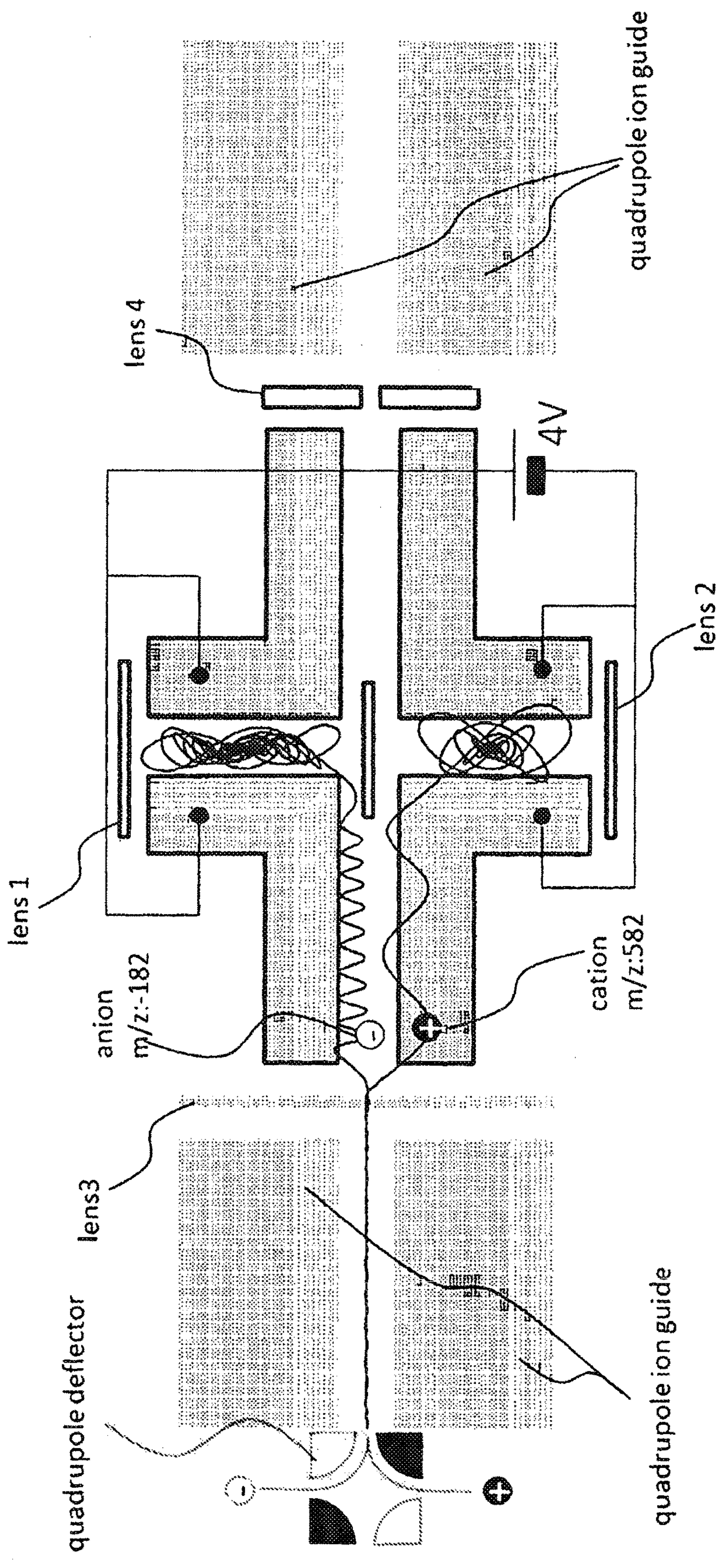
FIG. 5 is another view of the ion reaction device shown in FIG. 4A, depicting the paths along which exemplary anions and cation propagate to accumulate in the positive and negative ion trapping regions, FIG. 6A schematically depicts the ion reaction device in the step of ion processing in which the anions and the cations are simultaneously trapped in respective trapping regions.

With continued reference to FIG. 4A as well as FIGS. 4B and 5, during the ion accumulation phase, the axial trapping RF voltage is off, the lenses 3, 4, and 5 are grounded, and lenses 1 and 2 are biased via application of appropriate DC voltages, as discussed below. The DC dipolar electric field spatially separates the simultaneously injected cations and anions. More specifically, in this embodiment, the DC dipolar electric field causes the anions to move toward the set of electrodes held at a higher positive potential by the dipole DC voltage and the cations to move toward the other set of electrodes. In this example, the anions are assumed to have a an m/z of 182 and the cations are assumed to have an m/z of 582. As shown in FIG. 4B, the RF radial confinement voltages applied to the electrodes L1-L8 provide pseudo potentials with minima in proximity of the electrodes to ensure that the anions and cations move axially through the injection port 12*a* along radially separated paths without striking the electrode surfaces.

Once the ions reach the distal end of the injection port 12*a* (i.e., in the vicinity of the lens 5), the applied dipolar DC field causes the anions to enter the trapping port 18 and the cations to enter the trapping port 20. The application of DC voltages to lenses 1 and 2 can ensure that the anions and cations that enter the trapping ports 18 and 20 remain confined in those regions. In other words, the resultant electric fields apply forces to the ions that prevent them from leaving the trapping ports 18 and 20. By way of example, a negative DC voltage applied to the lens 1 (e.g., a voltage in a range of about 3 V to about 7 V) can generate an electric field that applies a repulsive force to the anions present in the trapping port 18 to prevent them from exiting the trapping port via the opening 18*b*. Further, a positive DC voltage applied to the lens 2 (e.g., a voltage in a range of about 3 V to about 7V) can generate an electric field that applies a repulsive force to the cations present in the trapping port 20 to prevent them from exiting the port via the opening 20*b*.

FIG. 4B schematically depicts RF pseudo potential and DC potential profiles during the accumulation step, indicating potential minima at the center of the trapping regions 18 and 20 for confining anions and cations, respectively. The anions and the cations continue to accumulate within the trapping ports 18 and 20 for a desired time period. In some embodiments, the accumulation step lasts for a time period in a range of about 1 to about 100 milliseconds (msec).

Figure 6A:
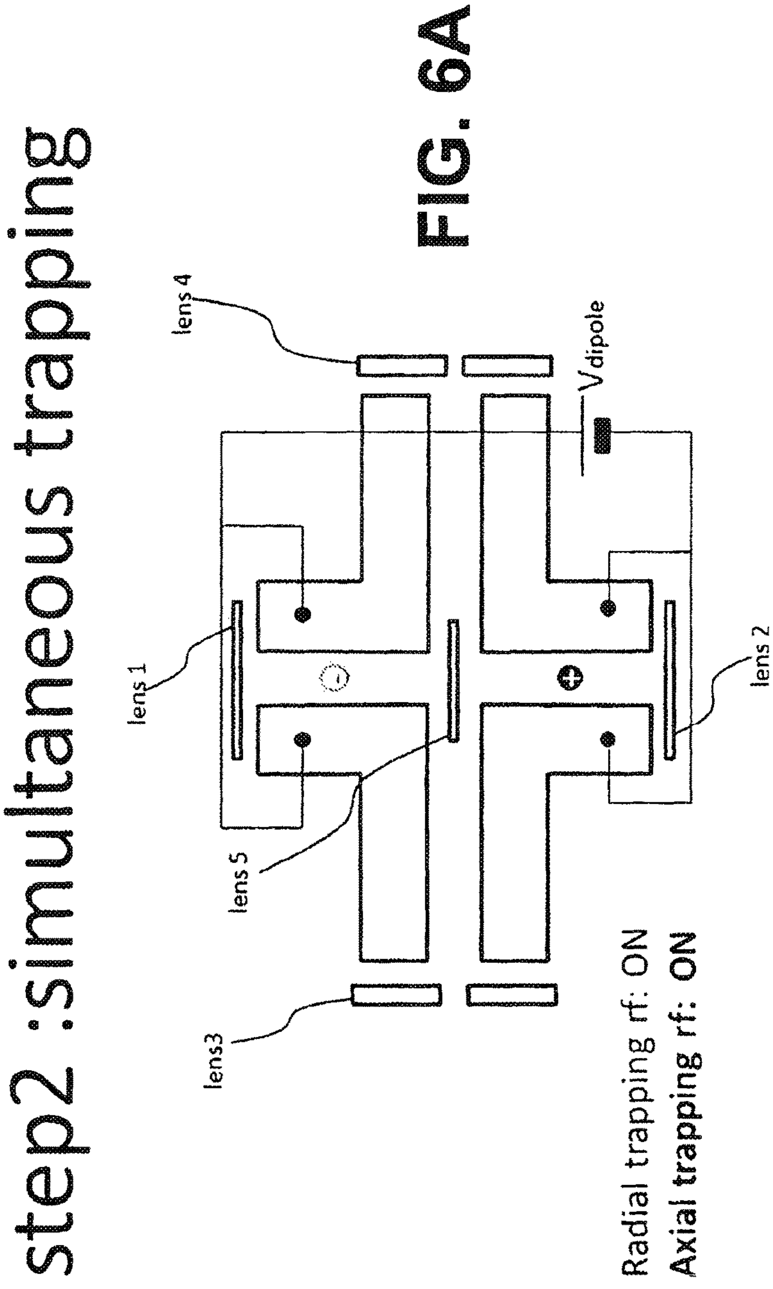
FIG. 6B shows RF and DC potential profiles employed in the ion processing step shown in FIG. 6A, FIG. 7A schematically depicts the ion reaction device in the step of ion processing in which the anions and the cations undergo ion-ion reactions.
Figure 6B:
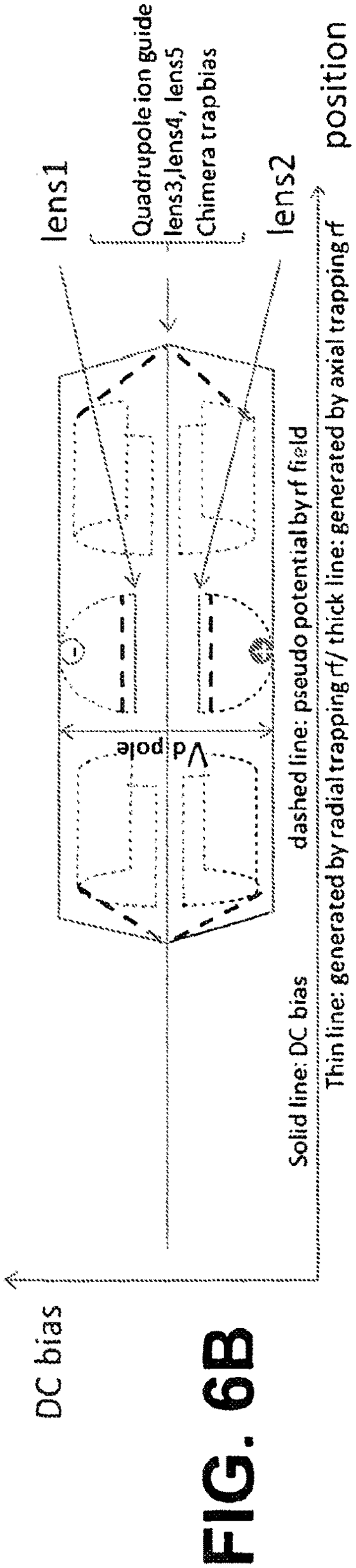

With reference to FIGS. 6A and 6B, in a subsequent step 2, the axial trapping RF is turned on while the lenses 3, 4, and 5 remain grounded. The lenses 1 and 2 are biased as in the previous step, and the DC dipole field remains on. In this step, the anions remain trapped in the trapping region 18 and the cations remain trapped in the trapping region 20. In other words, the negative and positive ions are simultaneously trapped in different regions of the reaction device 10. FIG. 6B shows the RF pseudo potential and the DC potential profiles that are present for simultaneously confining the negative and the positive ions in this step.

The trapping of ions within the trapping ports 18 and 20 according to the present teachings can advantageously prevent thermally induced dissociation (CID) of the ions because the trapped ions are stably confined by the quadrupole RF field without DC field in the radial direction.

Figure 7A:
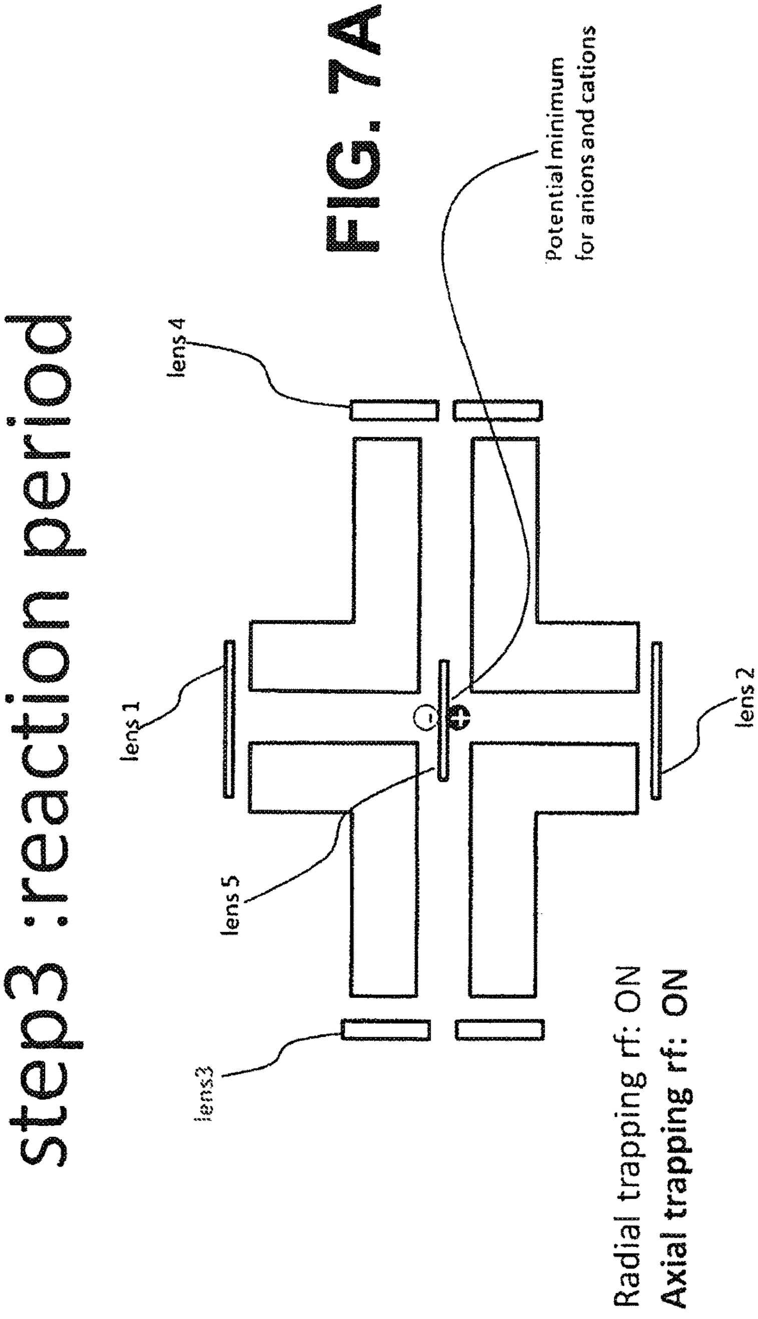
FIG. 7B shows RF and DC potential profiles employed during the ion-ion reaction phased depicted in FIG. 7A, FIG. 8A schematically depicts the ion reaction device in the ion processing step in which the anions are ejected from the device.
Figure 7B:
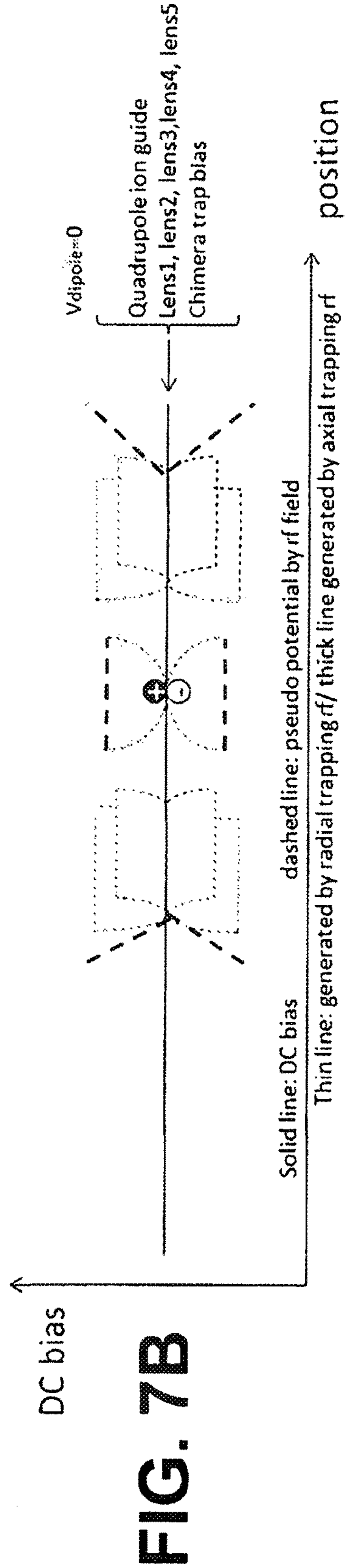

With reference to FIGS. 7A and 7B, in another step 3 (reaction period), the cations and anions are released from the trapping regions to mix with one another in the central region of the axial passage. More specifically, the dipole DC voltage is turned off, and the lenses 1-5 are grounded, while the radial and axial RF trapping voltages remain on. FIG. 7B schematically shows the RF pseudo potential as well as the DC potential profiles during this reaction step, illustrating potential minima in the central region of the axial passageway close to its longitudinal axis in which the anions and cations can fall to mix with one another.

In some embodiments, such mixing of the cations and anions can lead to electron transfer dissociation (ETD). The ETD processes can generate product ions through ionic interactions with oppositely charged reagent ions. In ETD, the electron is typically donated or lost through an ion/ion reaction of the precursor ion with a reagent ion of the opposite charge. In ETD, peptide and protein ion dissociation can give rise to product c- and z-type ions and preservation of post-translational modifications of the precursor peptides through extensive cleavage of the peptide backbone. In some embodiments, the mixing of the cations and anions can lead to proton transfer reaction (PTR), in which reagent anions can cause non-dissociative charge reduction of the precursor cations.

Figure 8A:
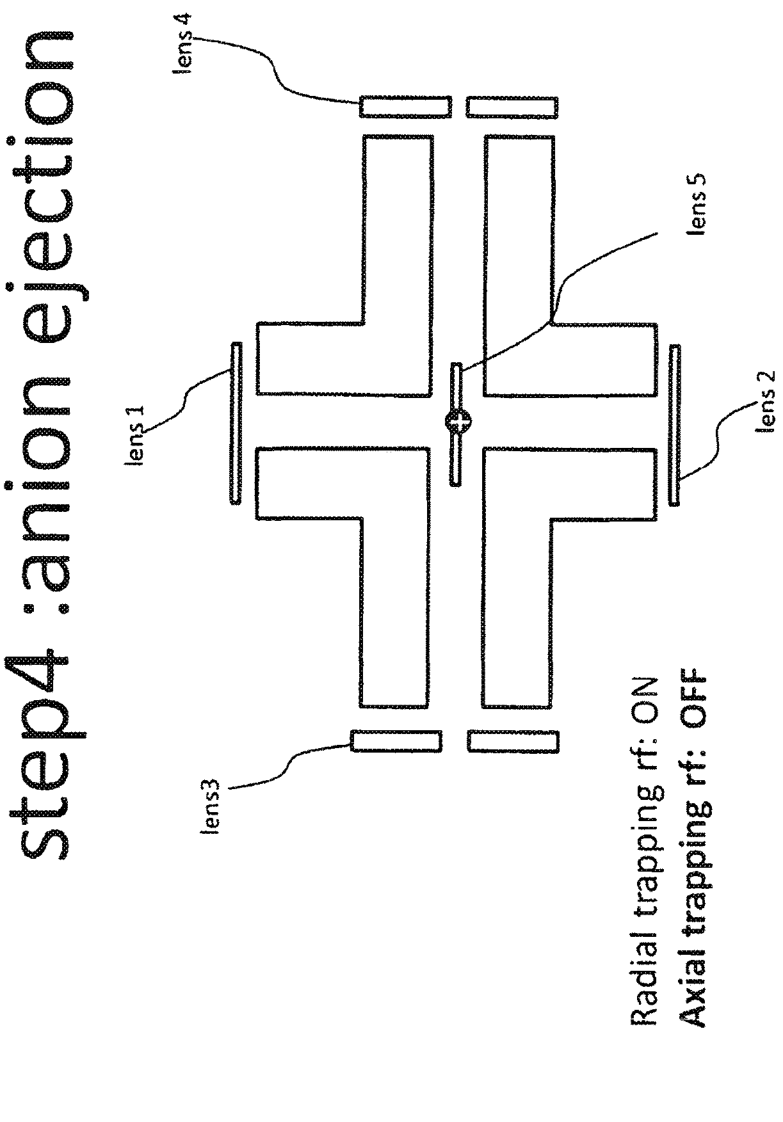
FIG. 8B shows RF and DC potential profiles employed during the ion processing step depicted in FIG. 8A, FIG. 9A schematically depicts the ion reaction device in the ion processing step in which product cations are extracted from the device.
Figure 8B:
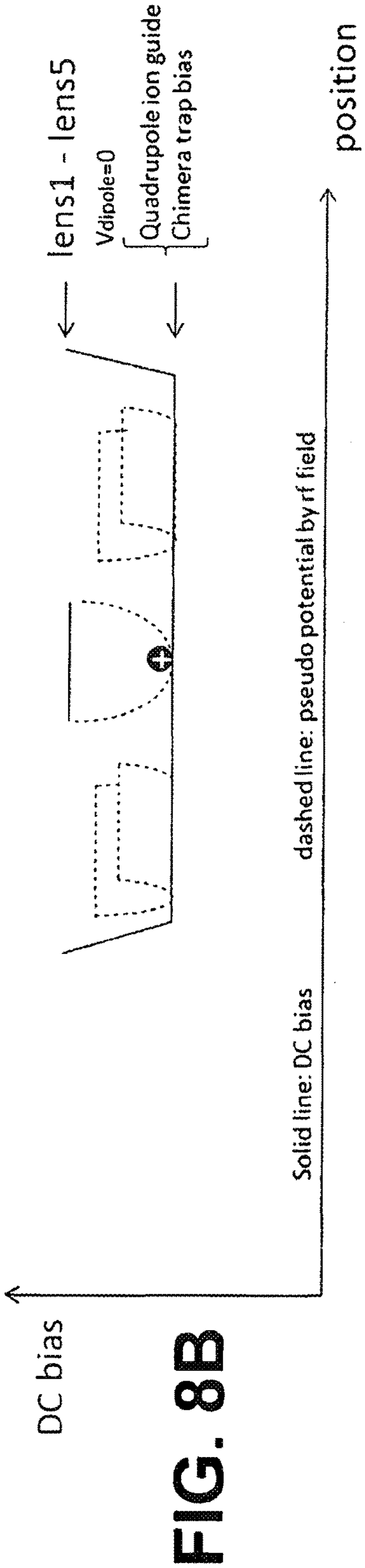

With reference to FIGS. 8A and 8B, in step 4, the anions are ejected from the reaction device 10. More specifically, the axial trapping RF voltage is turned off while the radial trapping RF remains on. Moreover, the lenses 1-5 are biased, via application of appropriate DC voltages thereto, to attract anions and repel cations. The resultant RF pseudo potential and DC potential profiles are shown in FIG. 8B. As shown in this figure, the cations continue to remain in the potential well at the center of the axial passage while the anions are attracted to the lenses 1-5 and are captured by that lens, and are thus removed.

Figure 9A:
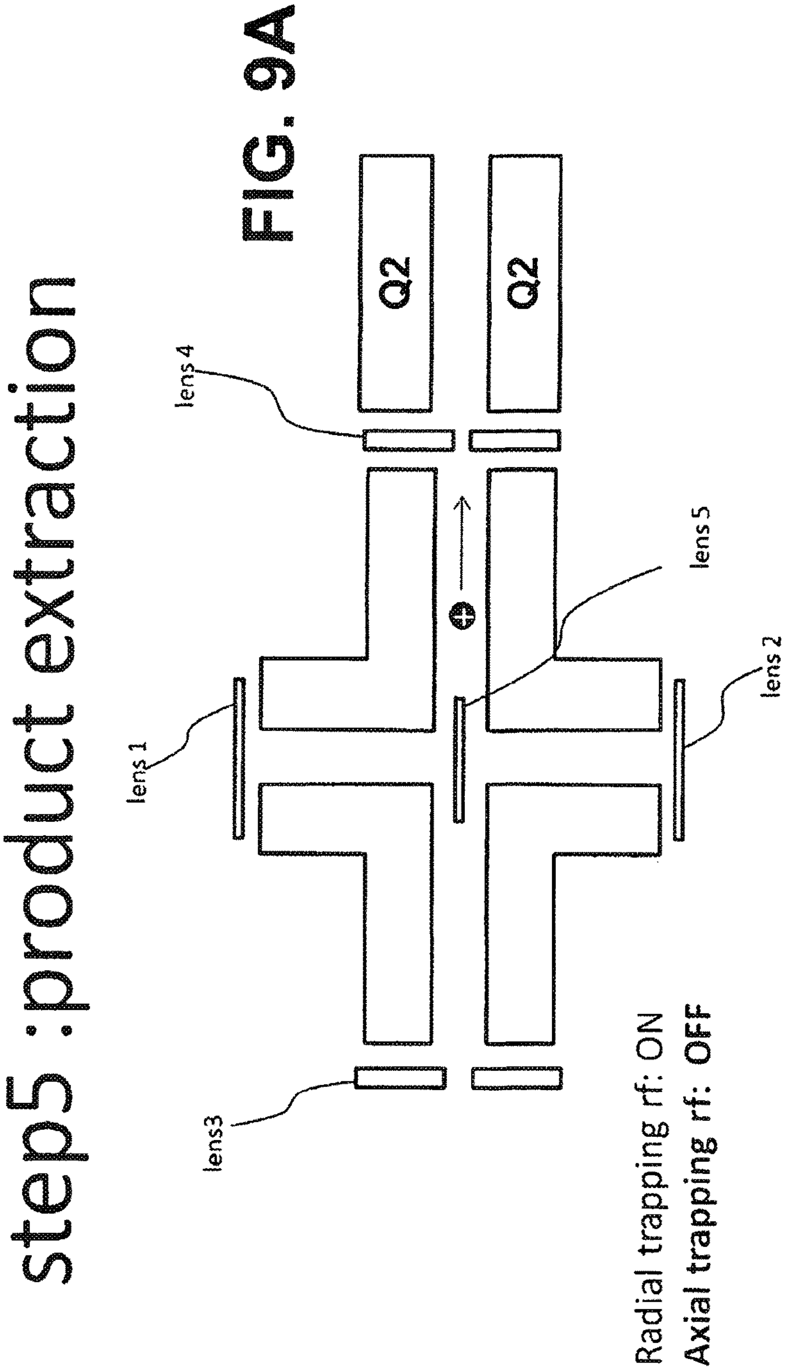
FIG. 9B shows RF and DC potential profiles employed during the ion processing step depicted in FIG. 9A, FIG. 10 schematically depicts an exemplary circuit for generating axial and radial RF voltages with the same frequency for application to the rods of the ion reaction device, FIG. 11 schematically depicts an exemplary circuit for generating axial and radial RF voltages with different frequencies for application to the rods of the ion reaction device, FIG. 12 schematically depicts an embodiment of the present teachings in which two quadrupole RF filters are employed to select anions and cations of interest for delivery to the ion reaction device, FIG. 13 schematically depicts an embodiment of an ion reaction device in accordance with the present teachings in which a quadrupole lens to which RF secular frequencies corresponding to anions and cations of interest is applied is employed for selecting those anions and cations for delivery to the reaction device.
Figure 9B:
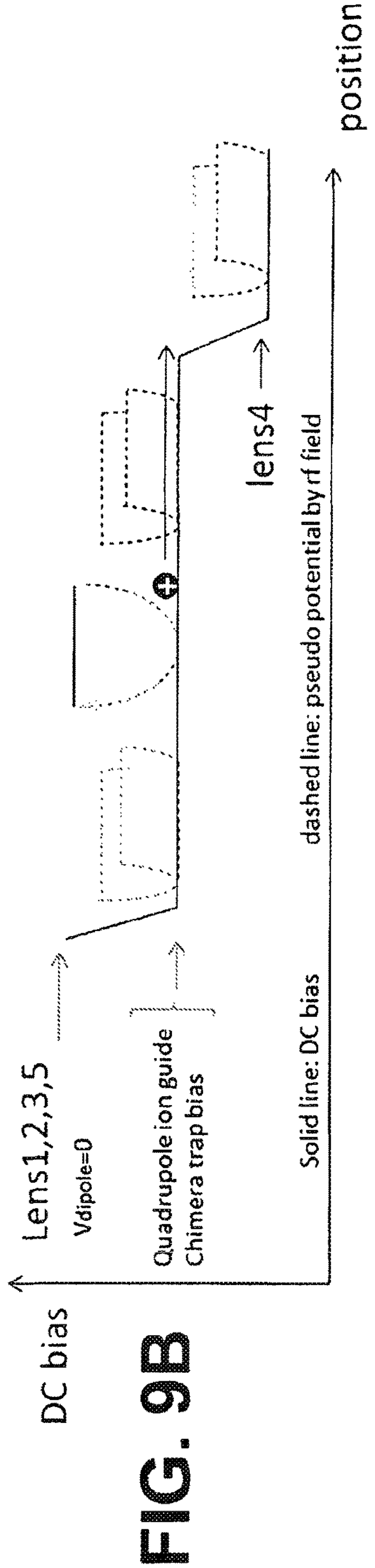

With reference to FIGS. 9A and 9B, in step 5 (product extraction), the positively charged product ions generated during the mixing step are extracted from the reaction device 10 and are transmitted to the downstream components of the spectrometer for analysis. More specifically, in this step, the axial trapping RF voltage remains off while the radial trapping RF voltage remains on. The lenses 1,2, 4, and 5 remain biased as in the previous step, while the polarity of DC bias applied to the lens 4 switches so as to generate an axial DC electric field for attracting the product cations into the ejection port 12*b* toward the lens 4. The resultant RF pseudo potential and DC potential profiles are shown in FIG. 9B, illustrating that the product cations move through the ejection port 12*b* to pass through the central orifice of the lens 4 and be received by a downstream ion lens Q2. The lens Q2, which can be for example an RF quadrupole lens, can guide the product ions to downstream elements, such as an analyzer.

Figure 10:
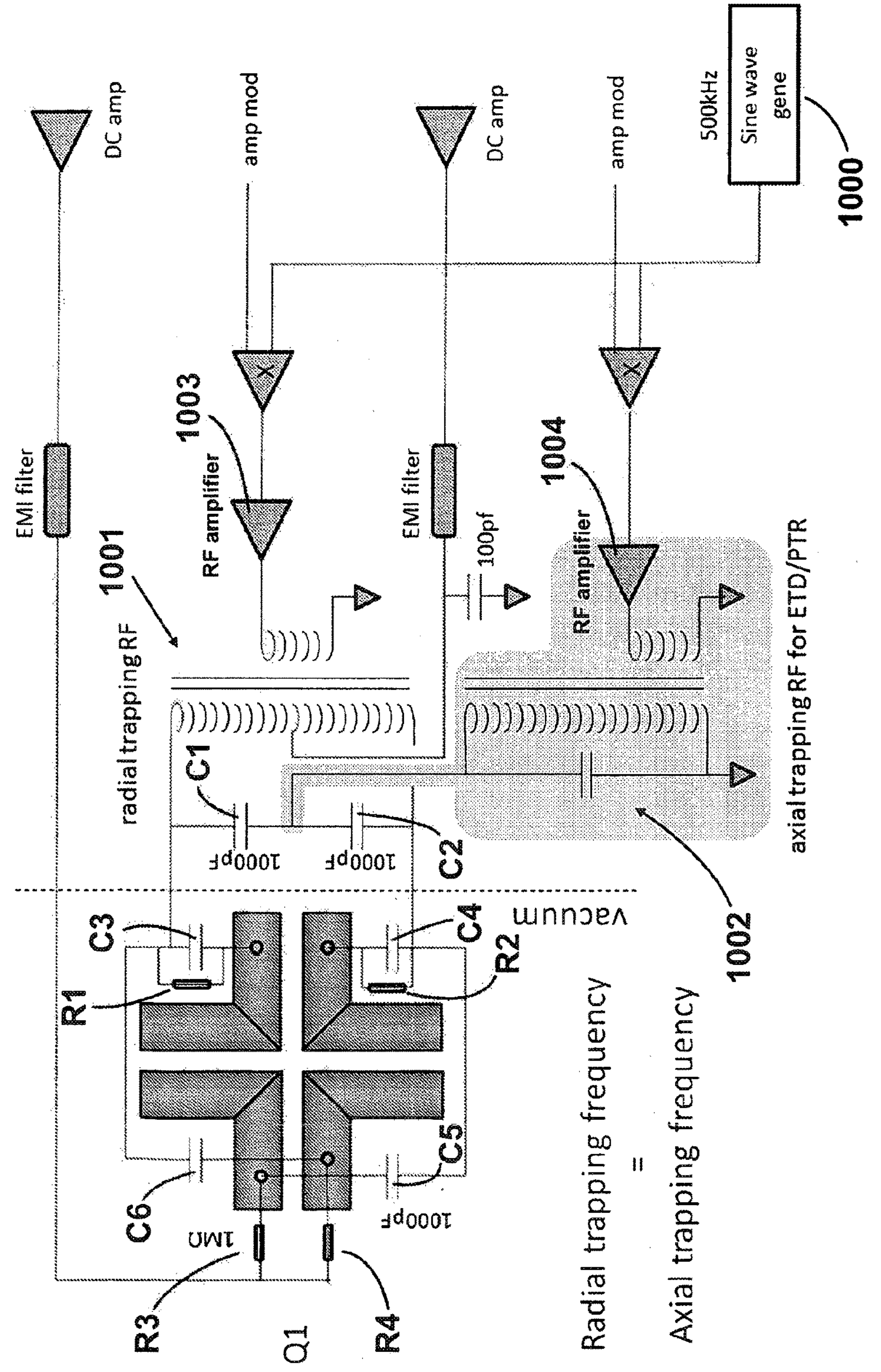

In some embodiments, the frequencies of the axial and radial trapping RF voltages applied to the electrodes L1-L8 can be the same. By way of example, FIG. 10 schematically depicts an exemplary circuit for generating axial and radial RF voltages with the same frequency. More specifically, a signal generator 1000, e.g., a sinusoidal wave generator in this example, generates an RF waveform having a frequency, for example, in a range of about 200 kHz to about 1 MHz (e.g., 500 kHz in this example). The waveform generated by the generator 1000 is applied to two transformers 1001 and 1002, via a plurality of amplifiers, such as RF amplifiers 1003 and 1004. The output of the transformer 1001 provides the RF radial trapping voltage and the output of the transformer 1002 provides the RF axial trapping voltages. A plurality of capacitors C3-C6 and a plurality of resistors R1-R4 are employed to apply both DC and RF voltages to different electrodes. In this embodiment, the axial trapping RF voltages applied to the electrodes have the same phase while the phases of the radial trapping RF voltages applied to the electrodes can vary between adjacent electrodes. The capacitors C1 and C2 are used for tuning of the resonant frequency. In some embodiments, the rms amplitudes of the axial and radial RF trapping voltages can be the same. In other embodiments, they can be different. For example, the ratios of the primary and secondary windings of the transformers can be adjusted to obtain different rms amplitudes for the axial and radial RF trapping voltages.

Figure 11:
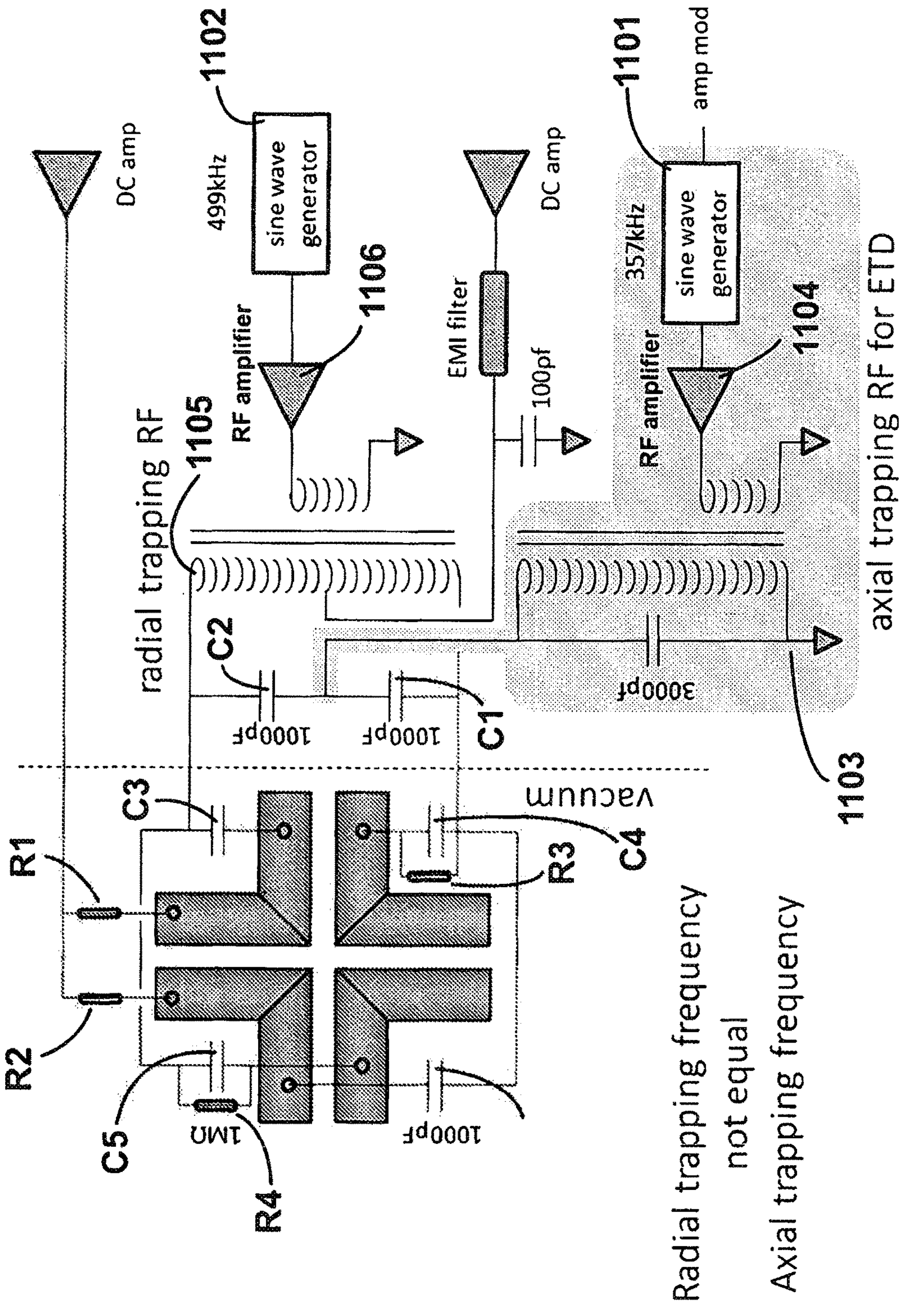

In other embodiments, the axial and the radial RF trapping voltages can have different frequencies. By way of example, FIG. 11 schematically depicts a circuit for generating axial and radial RF trapping voltages at different frequencies. Two RF signal generators 1101 and 1102 generate RF waveforms at different frequencies. In this example, the signal generator 1101 generates an RF waveform at a frequency of 357 kHz and the signal generator 1102 generates an RF waveform at a frequency of 499 kHz. The waveform generated by the generator 1101 is applied to a transformer 1103 via an RF amplifier 1104, and the waveform generated by the generator 1102 is applied to a transformer 1105 via an RF amplifier 1106. The output of the transformer 1105 provides the radial RF trapping voltage and the output of the transformer 1103 provides the axial RF trapping voltage. A plurality of capacitors C3-C6 and a plurality of resistors R1-R4 are employed to apply both DC and RF voltages to different electrodes. In this embodiment, the axial trapping RF voltages applied to the electrodes have the same phase while the phases of the radial trapping RF voltages applied to the electrodes can vary between adjacent electrodes. The capacitors C1 and C2 are used for tuning of the resonant frequency. In some embodiments, the rms amplitudes of the axial and radial RF trapping voltages can be the same. In other embodiments, they can be different. For example, the ratios of the primary and secondary windings of the transformers can be adjusted to obtain different rms amplitudes for the axial and radial RF trapping voltages.

Figure 12:
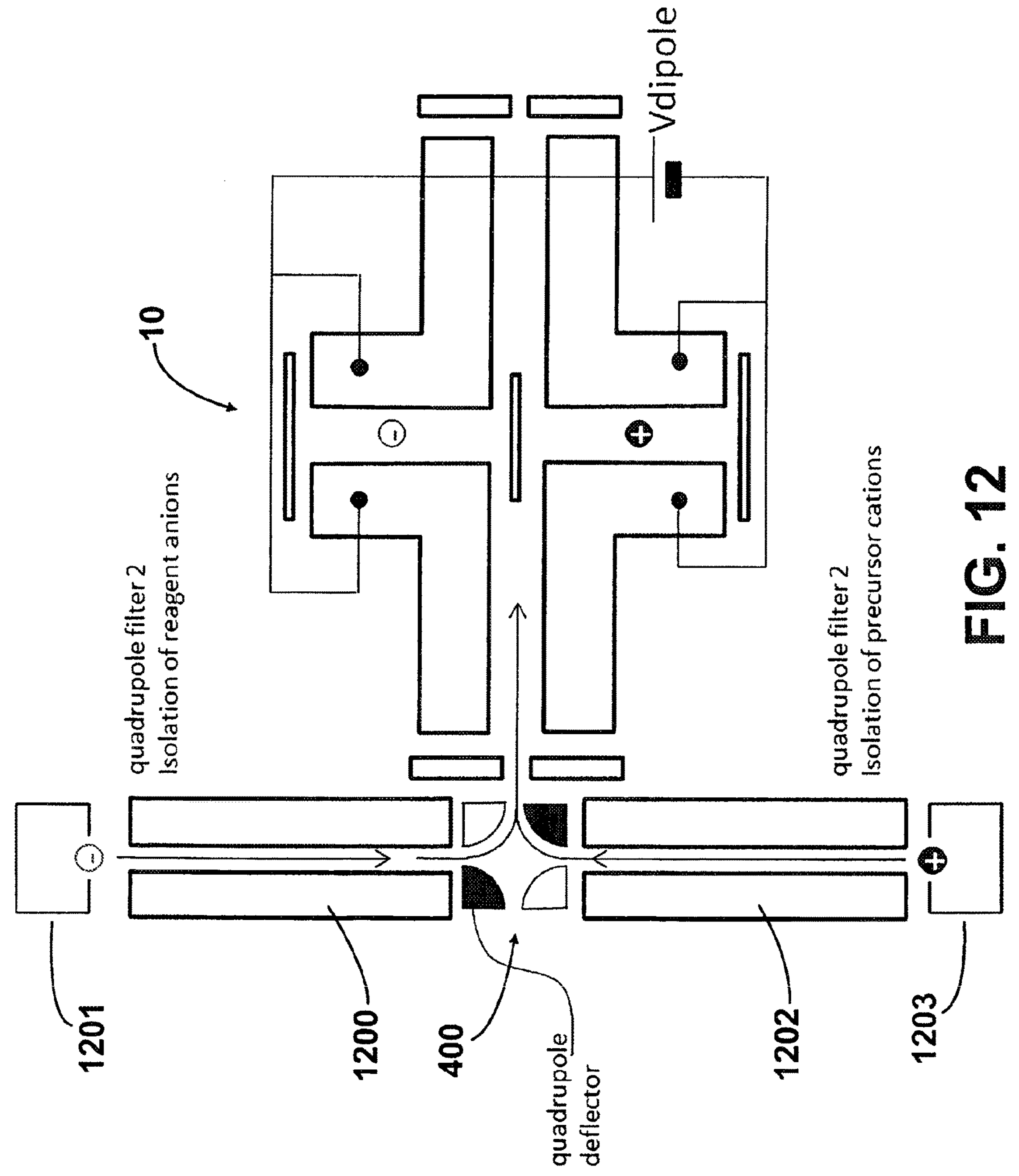

In some embodiments, one or more quadrupole mass filters can be disposed upstream of the reaction device to select anions and cations of interest from a plurality of different types of anions and cations generated by one or more ion sources (e.g., anions and cations having different m/z ratios). By way of example, FIG. 12 schematically depicts an embodiment of the present teachings in which a quadrupole RF filter 1200 receives a plurality of reagent anions from an ion source 1201, and another quadrupole RF filter 1202 receives a plurality of precursor cations from another ion source 1203.

The quadrupole RF filter 1200 can be configured, via application of appropriate RF voltages to its rods, to provide stable trajectories for the passage of anions of interest having a desired m/z ratio or an m/z ratio within a particular range, and to filter out the other anions by subjecting them to unstable trajectories. Similarly, the quadrupole RF filter 1202 can be configured, via application of appropriate RF voltages to its rods, to provide stable trajectories for the passage of cations of interest having a desired m/z ratio or an m/z ratio within a particular range, and to filter out the other cations by subjecting them to unstable trajectories.

The anions and cations pass through the RF filters 1200 and 1203, respectively, and enter the quadrupole DC deflector 400 and are deflected into the reaction device 10 in a manner discussed above in connection with the previous embodiments.

Figure 13:
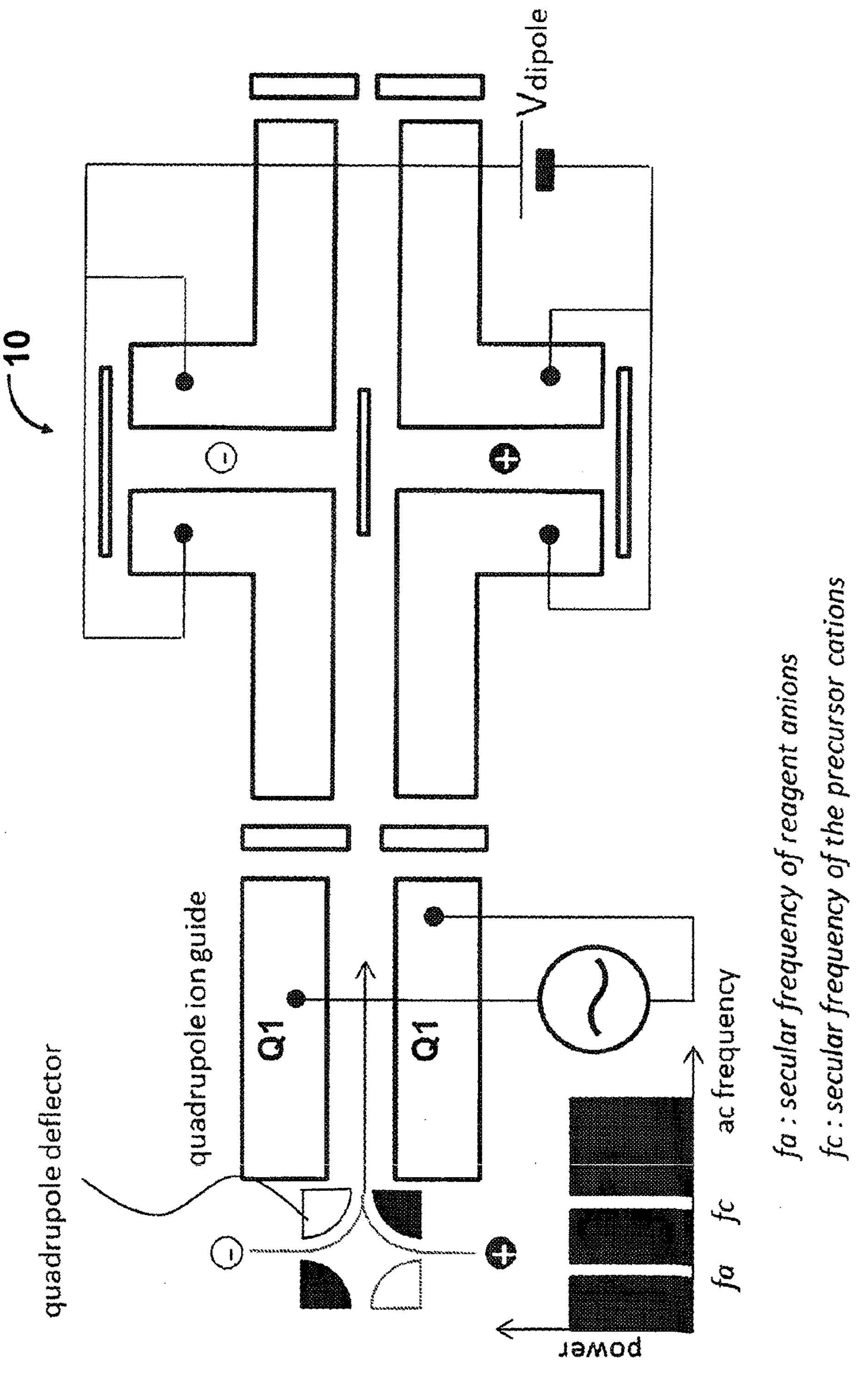

In some embodiments, an RF quadrupole filter disposed downstream of a DC deflector, which is configured to receive ions from a plurality of ion sources, and upstream of an ion reaction device according to the present teachings can be configured to allow the passage of particular anions and cations of interest while filtering out the rest. By way of example, FIG. 13 shows such an embodiment in which, similar to the embodiment discussed above in connection with FIGS. 4B and 5, a quadrupole ion guide Q1 is disposed between the ion deflector 400 and the ion reaction device 10. The RF frequencies applied to the quadrupole rods of the ion guide Q1 are selected to correspond to the secular frequencies ($f_a$) and ($f_c$) of the reagent anions and precursor cations of interest, respectively. In other words, the secular frequency $f_a$ can provide stable trajectories for reagent anions having m/z ratios in a desired range (or a specific value) and the secular frequency $f_c$ can provide stable trajectories of precursor cations having m/z ratios in a desired range (or a specific value). In this manner, the reagent anions and precursor cations of interest are transmitted to the downstream ion reaction device 10 to be processed in a manner discussed above.

In some embodiments, rather than employing two ion sources, a single ion source can be employed to generate both the anions and cations. For example, the reagent and precursor molecules can be alternatively introduced into the ion source and the polarity of voltages employed in the ion source can be switched in different time periods such that during one time period, cations of the precursor ions are generated and in another time period anions of the reagent molecules are produced.

Those having ordinary skill in the art will appreciate that various changes can be made to the above embodiments without departing from the scope of the invention.

What is claimed is:

1. An ion reaction device, comprising:

an ion injection inlet for receiving a plurality of ions and an ion ejection outlet through which ions can exit the device, a plurality of non-linear rods disposed relative to one another so as to provide an axial region configured to receive a plurality of anions and cations via said ion injection inlet, and a plurality of trapping regions in communication with the axial region in which said anions and cations can be confined, the plurality of non-linear rods defining a pair of quadrupole rod sets wherein said quadrupole rod sets are stacked relative to one another so as that each non-linear rod in one of said quadrupole rod sets is disposed below a respective non-linear rod of the other of the pair of quadrupole rod sets and in substantial register therewith, each of the non-linear rods includes a longitudinal portion and a transverse portion forming an angle relative to the longitudinal portion, the axial region being spatially defined by the longitudinal portions of the non-linear rods, and the plurality of trapping regions comprise two trapping regions spatially defined by said transverse portion of the non-linear rods, each of said two trapping regions extending from a proximal opening in communication with said axial region to a distal opening, and a DC voltage source adapted to apply a DC voltage across at least two of said non-linear rods so as to generate a dipolar electric field within at least a portion of said axial region for spatially separating the received anions and cations and guiding said anions into one of said two trapping regions and the cations into the other of said two trapping regions, first and second lenses, wherein one of said lenses is disposed in proximity of said distal opening of the two trapping regions and the other one of said lenses is disposed in proximity of said distal opening of the other of the two trapping regions, said lenses being adapted for application of DC bias voltages thereto for facilitating trapping of the anions and cations in the respective two trapping regions.

2. The ion reaction device of claim 1, wherein said non-linear rods are L-shaped rods.

3. The ion reaction device of claim 1, further comprising a third lens disposed upstream of said plurality of rods and adapted for application of a DC voltage thereto, wherein said third lens comprises a plate having an orifice forming said ion injection inlet.

4. The ion reaction device of claim 3, further comprising a fourth lens dispose downstream of said plurality of rods and adapted for application of a DC voltage thereto, wherein said fourth lens comprises a plate having an orifice forming said ion ejection outlet.

5. The ion reaction device of claim 4, further comprising a fifth lens disposed in said axial region in proximity to said proximal openings of said trapping regions.

6. An ion reaction device, comprising:

an ion injection inlet for receiving a plurality of ions and an ion ejection outlet through which ions can exit the device, a plurality of non-linear rods disposed relative to one another so as to provide an axial region configured to receive a plurality of anions and cations via said ion injection inlet, and a plurality of trapping regions in communication with the axial region in which said anions and cations can be confined, the plurality of non-linear rods defining a pair of quadrupole rod sets and a DC voltage source adapted to apply a DC voltage across at least two of said non-linear rods so as to generate a dipole electric field within at least a portion of said axial region for spatially separating the received anions and cations and guiding said anions into one of said trapping regions and the cations into another one of said trapping regions, wherein said DC voltage source is connected at one of one terminal to a subset of said non-linear rods and at another terminal to another subset of said non-linear rods so as to generate the dipole electric field in at least a portion of said axial region, and each terminal thereof to two non-linear rods of one of said pair of quadrupole rod sets and to two non-linear rods of the other of said pair of quadrupole rod sets, where said two non-linear rods of one of said pair of quadrupole rod set are vertically stacked relative to said two non-linear rods of the other of said pair of quadrupole rod sets, so as to generate the dipole electric field in at least a portion of said axial region.

7. The ion reaction device of claim 1, further comprising a first RF source for applying RF voltages to said non-linear rods configured to provide radial confinement of said anions and cations.

8. The ion reaction device of claim 7, further comprising a second RF source for applying RF voltages to said non-linear rods configured to provide axial confinement of said anions and cations.

9. The ion reaction device of claim 8, wherein said first and second RF sources are configured to apply RF voltages having the same frequencies to said non-linear rods.

10. The ion reaction device of claim 8, wherein said first and second RF sources are configured to apply RF voltages having different frequencies to said non-linear rods.

11. A mass spectrometer, comprising:

a plurality of ion sources, wherein at least one of said sources is adapted to generate anions and another of said sources is adapted to generate cations, an ion reaction device configured to receive said anions and cations, said reaction device comprising an ion injection inlet for receiving a plurality of ions and an ion ejection outlet through which ions can exit the device, a plurality of non-linear rods disposed relative to one another so as to provide an axial region configured to receive a plurality of anions and cations via said ion injection inlet, and a plurality of trapping regions in communication with the axial region in which said anions and cations can be confined, and a DC voltage source adapted to apply a DC voltage across at least two of said non-linear rods so as to generate a dipolar electric field within at least a portion of said axial region for spatially separating the received anions and cations and guiding said anions into one of said trapping regions and the cations into another one of said trapping regions, a DC deflector disposed upstream of said reaction device, said deflector having first and second inlet ports for receiving, respectively, said anions and cations from said ion sources and having an outlet port in communication with said reaction device, wherein said DC deflector is configured to guide said received anions and cations to said outlet port, wherein said DC deflector comprises a quadrupole DC deflector.

12. The mass spectrometer of claim 11, further comprising a quadrupole lens disposed between said DC deflector and said reaction device for selecting cations and anions having an m/z ratio in a desired range.

13. The mass spectrometer of claim 11, further comprising a quadrupole lens disposed between said sources for generating one of anions and cations and said DC deflector for selecting one of anions and cations having an m/z ratio in a desired range for delivery to said DC deflector.

14. An ion reaction device for use in a mass spectrometer, comprising:

a plurality of non-linear electrodes each of which includes a longitudinal segment and a transverse segment forming a non-zero angle with the longitudinal segment, said electrodes being disposed relative to one another such that longitudinal segments of the electrodes provide an axial region therebetween having an ion injection port for receiving a plurality of anions and cations from one or more upstream ion sources and the transverse segment provide a plurality of regions in which ions can be trapped, a DC voltage source configured to apply a voltage across at least two of said electrodes so as to generate a dipolar DC electric field in at least a portion of said axial region for spatially separating the anions and the cations as they propagate through said injection port and to guide said anions into one of said trapping regions and said cations into another one of said trapping regions.

* * * * *